(12) United States Patent
Labit et al.

(10) Patent No.: US 8,777,915 B2
(45) Date of Patent: *Jul. 15, 2014

(54) REUSABLE DIAPERS HAVING SEAM ALLOWANCES

(76) Inventors: Jennifer Lynn Labit, Arnold, MO (US); James Andrew Labit, Arnold, MO (US)

( * ) Notice: Subject to any disclaimer, the term of this patent is extended or adjusted under 35 U.S.C. 154(b) by 496 days.

This patent is subject to a terminal disclaimer.

(21) Appl. No.: 13/246,647

(22) Filed: Sep. 27, 2011

(65) Prior Publication Data

US 2012/0016333 A1     Jan. 19, 2012

Related U.S. Application Data

(63) Continuation of application No. 12/059,844, filed on Mar. 31, 2008, now Pat. No. 8,062,276, which is a continuation-in-part of application No. 11/518,587, filed on Sep. 8, 2006, now Pat. No. 7,629,501.

(51) Int. Cl.
| | |
|---|---|
| *A61F 13/15* | (2006.01) |
| *A61F 13/56* | (2006.01) |
| *A61F 13/493* | (2006.01) |
| *A61F 13/505* | (2006.01) |
| *A61F 13/49* | (2006.01) |

(52) U.S. Cl.
CPC ....... *A61F 13/49004* (2013.01); *A61F 13/5622* (2013.01); *A61F 13/493* (2013.01); *A61F 13/505* (2013.01)
USPC ............ 604/385.15; 604/385.14; 604/385.01; 604/385.101

(58) Field of Classification Search
USPC ......................... 604/385.01, 385.101, 385.15, 604/385.22–385.26
See application file for complete search history.

(56) References Cited

U.S. PATENT DOCUMENTS

| | | |
|---|---|---|
| 1,003,399 A | 9/1911 | Burns |
| 1,961,515 A | 6/1934 | Friedman |

(Continued)

FOREIGN PATENT DOCUMENTS

| | | |
|---|---|---|
| AU | 5039493 | 1/1994 |
| AU | 9539089 | 6/1996 |

(Continued)

OTHER PUBLICATIONS

First Office Action from Canadian application No. 2,632,792, dated Jul. 31, 2013, which claims priority to the same parent U.S. Appl. No. 12/059,844, filed Mar. 31, 2008 (now U.S. Patent No. 8,062,276, granted Nov. 22, 2011) as the instant application; 3 pages.

(Continued)

*Primary Examiner* — Michele M Kidwell
(74) *Attorney, Agent, or Firm* — Harness, Dickey & Pierce, PLC

(57) ABSTRACT

A reusable diaper may include an inner layer to wick moisture and an outer layer substantially impervious to liquids. A waist portion may include a corner region for securing the diaper in a desired position. The corner region may be resiliently stretchable and substantially impervious to liquids, and may include first and second layers coupled to the respective inner and outer layers. The coupled first layer and inner layer define a first seam allowance, and the coupled second layer and outer layer define a second seam allowance. The first and second seam allowances may be positioned within the corner region to help inhibit wicking of liquid through the seam allowances into the corner region. And a fluid-resistant region may be provided to help resist wicking of moisture through the inner layer past the fluid-resistant region.

24 Claims, 11 Drawing Sheets

(56) References Cited

U.S. PATENT DOCUMENTS

| | | |
|---|---|---|
| 2,016,355 A | 10/1935 | Alsop |
| 2,049,913 A | 8/1936 | Lesueur |
| RE20,315 E | 3/1937 | Lesueur |
| 2,292,030 A | 8/1942 | Kraft |
| 2,450,059 A | 9/1948 | Rickerson |
| 2,468,445 A | 4/1949 | Hurst |
| 2,493,492 A | 1/1950 | Malamut |
| 2,523,079 A | 9/1950 | Walter et al. |
| 2,532,029 A | 11/1950 | Medoff |
| 2,545,216 A | 3/1951 | Toussie |
| 2,568,590 A | 9/1951 | Laser |
| 2,575,164 A | 11/1951 | Donovan |
| 2,577,398 A | 12/1951 | Blake |
| 2,581,904 A | 1/1952 | Burns |
| 2,591,079 A | 4/1952 | Leaton |
| 2,606,558 A | 8/1952 | Kennette |
| 2,607,348 A | 8/1952 | Rosenblatt |
| 2,627,859 A | 2/1953 | Hargrave |
| 2,664,895 A | 1/1954 | Shulman |
| 2,688,328 A | 9/1954 | Marcus |
| 2,703,577 A | 3/1955 | May |
| 2,733,715 A | 2/1956 | Folk |
| 2,788,786 A | 4/1957 | Dexter |
| 2,826,199 A | 3/1958 | Brandon |
| 2,853,073 A | 9/1958 | Brafman |
| 2,866,459 A | 12/1958 | Sobelson |
| 2,868,205 A | 1/1959 | Epstein |
| 2,893,393 A | 7/1959 | Pressley |
| 2,910,982 A | 11/1959 | Woodward |
| 2,985,170 A | 5/1961 | Title |
| 3,049,124 A | 8/1962 | Thompson |
| 3,141,461 A | 7/1964 | Farris |
| 3,162,196 A | 12/1964 | Salk |
| 3,341,394 A | 9/1967 | Kinney |
| 3,485,706 A | 12/1969 | Evans |
| 3,530,859 A | 9/1970 | Helmowitz |
| 3,559,648 A | 2/1971 | Mason, Jr. |
| 3,658,064 A * | 4/1972 | Pociluyko .................. 604/360 |
| 3,667,466 A | 6/1972 | Ralph |
| 3,741,212 A | 6/1973 | Schutte |
| 3,769,978 A | 11/1973 | DeNight et al. |
| 3,882,871 A | 5/1975 | Taniguchi |
| RE28,483 E | 7/1975 | Ralph |
| 3,926,189 A | 12/1975 | Taylor |
| 4,037,602 A | 7/1977 | Hawthorne |
| 4,338,939 A | 7/1982 | Daville |
| D269,907 S | 7/1983 | Tong |
| 4,414,971 A | 11/1983 | Chung et al. |
| 4,548,604 A | 10/1985 | Ellsworth |
| 4,568,342 A | 2/1986 | Davis |
| 4,573,987 A | 3/1986 | Lamb, Jr. |
| 4,643,726 A | 2/1987 | Gegelys |
| 4,671,793 A | 6/1987 | Hults et al. |
| 4,681,581 A | 7/1987 | Coates |
| 4,695,279 A | 9/1987 | Steer |
| 4,704,117 A | 11/1987 | Mitchell |
| 4,773,906 A | 9/1988 | Krushel |
| 4,834,737 A | 5/1989 | Khan |
| 4,850,987 A | 7/1989 | Gilomen et al. |
| 4,892,598 A | 1/1990 | Stevens et al. |
| 4,904,251 A | 2/1990 | Igaue et al. |
| 4,906,243 A | 3/1990 | Dravland |
| 4,928,323 A | 5/1990 | Nathan |
| 4,950,263 A | 8/1990 | Lewis |
| 4,961,736 A * | 10/1990 | McCloud ................ 604/385.15 |
| 4,978,345 A | 12/1990 | Holiday et al. |
| 4,981,480 A | 1/1991 | Gaudet et al. |
| 5,019,068 A | 5/1991 | Perez et al. |
| 5,069,672 A | 12/1991 | Wippler et al. |
| 5,100,399 A | 3/1992 | Janson et al. |
| 5,106,382 A | 4/1992 | Henry |
| 5,108,385 A | 4/1992 | Snyder |
| 5,135,522 A | 8/1992 | Fahrenkrug et al. |
| 5,137,526 A | 8/1992 | Coates |
| 5,185,011 A | 2/1993 | Strasser |
| 5,188,626 A | 2/1993 | Toyoda et al. |
| 5,207,662 A | 5/1993 | James |
| 5,217,447 A | 6/1993 | Gagnon |
| D339,633 S | 9/1993 | Porter |
| 5,304,162 A | 4/1994 | Kuen |
| 5,306,267 A | 4/1994 | Hahn et al. |
| 5,325,543 A | 7/1994 | Allen |
| 5,342,340 A | 8/1994 | Kichefski et al. |
| 5,360,422 A | 11/1994 | Brownlee et al. |
| D354,809 S | 1/1995 | Eskey |
| 5,399,177 A | 3/1995 | Blaney et al. |
| 5,405,342 A | 4/1995 | Roessler et al. |
| 5,409,476 A | 4/1995 | Coates |
| D362,717 S | 9/1995 | Caschette et al. |
| 5,454,799 A | 10/1995 | Lakiss-Smith et al. |
| 5,458,591 A | 10/1995 | Roessler et al. |
| 5,476,457 A | 12/1995 | Roessler et al. |
| D366,112 S | 1/1996 | Tollin et al. |
| 5,514,121 A | 5/1996 | Roe et al. |
| 5,527,300 A | 6/1996 | Sauer |
| 5,611,789 A | 3/1997 | Seth |
| 5,613,959 A | 3/1997 | Roessler et al. |
| 5,635,275 A | 6/1997 | Biagioli et al. |
| D386,582 S | 11/1997 | Levine |
| 5,695,488 A | 12/1997 | Sosalla |
| 5,706,524 A | 1/1998 | Herrin et al. |
| 5,722,127 A | 3/1998 | Coates |
| 5,725,518 A | 3/1998 | Coates |
| 5,814,037 A | 9/1998 | Coates |
| 5,853,403 A | 12/1998 | Tanzer et al. |
| 5,891,122 A | 4/1999 | Coates |
| D436,400 S | 1/2001 | Kiecker |
| 6,168,583 B1 | 1/2001 | Tanji et al. |
| 6,193,702 B1 | 2/2001 | Spencer |
| 6,254,583 B1 | 7/2001 | Coates |
| 6,315,764 B1 | 11/2001 | Faulks et al. |
| 6,322,552 B1 | 11/2001 | Blenke et al. |
| 6,379,343 B2 | 4/2002 | Stephenson et al. |
| 6,383,170 B1 | 5/2002 | Mishima et al. |
| 6,401,250 B1 | 6/2002 | McNabb |
| 6,402,731 B1 | 6/2002 | Surprise et al. |
| 6,423,047 B1 | 7/2002 | Webster |
| 6,471,681 B1 | 10/2002 | Ronnberg et al. |
| 6,482,194 B1 | 11/2002 | Putzer |
| 6,540,730 B1 | 4/2003 | Niedermeyer |
| 6,562,016 B2 | 5/2003 | Shinkai |
| 6,569,137 B2 | 5/2003 | Suzuki et al. |
| 6,579,273 B2 | 6/2003 | Dupuy |
| 6,616,645 B1 | 9/2003 | Moravek |
| 6,623,466 B1 | 9/2003 | Richardson |
| 6,639,041 B2 | 10/2003 | Nishikawa et al. |
| 6,641,569 B1 | 11/2003 | Coles et al. |
| 6,766,817 B2 | 7/2004 | da Silva et al. |
| 6,767,498 B1 | 7/2004 | Talley et al. |
| 6,918,404 B2 | 7/2005 | Dias da Silva et al. |
| 6,932,800 B2 | 8/2005 | LaVon et al. |
| 6,989,005 B1 | 1/2006 | LaVon et al. |
| 7,066,586 B2 | 6/2006 | da Silva et al. |
| 7,244,398 B2 | 7/2007 | Kotary et al. |
| 7,264,615 B2 | 9/2007 | Sherrod et al. |
| 7,285,255 B2 | 10/2007 | Kadlec et al. |
| 7,361,803 B2 | 4/2008 | Miskie |
| 7,591,811 B2 | 9/2009 | Crislip Wilkinson |
| 7,629,501 B2 | 12/2009 | Labit et al. |
| 2002/0010452 A1 | 1/2002 | Dupuy |
| 2002/0094740 A1 | 7/2002 | Li et al. |
| 2003/0014024 A1 | 1/2003 | Kiecker |
| 2003/0083635 A1 | 5/2003 | Gibbs |
| 2003/0109841 A1 | 6/2003 | Edwards |
| 2004/0002691 A1 | 1/2004 | Popp et al. |
| 2004/0044323 A1 | 3/2004 | Roessler et al. |
| 2004/0082933 A1 | 4/2004 | Karami |
| 2004/0236298 A1 | 11/2004 | Coates |
| 2004/0236300 A1 | 11/2004 | Gibbs et al. |
| 2004/0267219 A1 | 12/2004 | Olmedo |
| 2005/0085784 A1 | 4/2005 | LeMinh et al. |
| 2005/0148258 A1 | 7/2005 | Chakravarty et al. |
| 2005/0210560 A1 | 9/2005 | Coates |
| 2005/0228356 A1 | 10/2005 | LaVon et al. |

(56) References Cited

U.S. PATENT DOCUMENTS

| | | |
|---|---|---|
| 2006/0167432 A1 | 7/2006 | Sigari |
| 2007/0066952 A1 | 3/2007 | LaVon et al. |
| 2008/0015531 A1 | 1/2008 | Hird et al. |
| 2008/0065039 A1 | 3/2008 | Labit et al. |
| 2008/0183148 A1 | 7/2008 | Labit et al. |
| 2010/0036340 A1 | 2/2010 | Allison-Rogers |
| 2010/0036353 A1 | 2/2010 | Payne |
| 2010/0087794 A1 | 4/2010 | Labit et al. |
| 2010/0108554 A1 | 5/2010 | Melius et al. |
| 2010/0130955 A1 | 5/2010 | Tice |
| 2011/0137278 A1 | 6/2011 | Ormsby et al. |
| 2011/0319852 A1 | 12/2011 | Labit |

FOREIGN PATENT DOCUMENTS

| | | |
|---|---|---|
| BR | 03606/71 | 12/1971 |
| BR | 360571 | 12/1971 |
| CA | 2024375 | 3/1992 |
| CA | 2097437 | 12/1993 |
| CA | 2103537 A | 2/1995 |
| DE | 4326271 | 2/1995 |
| DE | 10303903 | 11/2003 |
| EP | 0099846 | 2/1984 |
| EP | 0486006 | 11/1991 |
| EP | 0475702 | 3/1992 |
| EP | 2106775 | 10/2009 |
| ES | 2115559 | 6/1998 |
| GB | 493819 | 10/1938 |
| GB | 0849573 | 9/1960 |
| GB | 0803716.0 | 2/2008 |
| JP | 04150853 | 5/1992 |
| JP | 08000662 | 1/1996 |
| WO | WO-87/05471 | 9/1987 |
| WO | WO-90/07313 | 7/1990 |
| WO | WO-94/03137 | 2/1994 |
| WO | WO 94/15563 | 7/1994 |
| WO | WO-95/23569 | 9/1995 |
| WO | WO-98/24388 | 6/1998 |
| WO | WO-99/33421 | 7/1999 |
| WO | WO-2008/030984 | 3/2008 |
| WO | WO-2008/142634 | 11/2008 |
| WO | WO-2009/106899 | 9/2009 |
| WO | WO-2009/146021 | 12/2009 |
| ZA | 8701842 | 11/1988 |

OTHER PUBLICATIONS

Biodegradable Diapers, Real user reviews of Biodegradable Diapers, diapers that are good for babies, parents and the planet, CuteyBaby "One and Done!" Modern Cloth Diaper Starter Kit—Girl, 5 pages, (Customer Review, Mar. 22, 2011) biodegradablediapers.info.

Biodegradable Diapers, Real user reviews of Biodegradable Diapers, diapers that are good for babies, parents and the planet, CuteyBaby "One and Done!" Modern Cloth Diaper Starter Kit—Girl, 5 pages, (Customer Review, Jun. 3, 2010) biodegradablediapers.info.

Biodegradable Diapers, Real user reviews of Biodegradable Diapers, diapers that are good for babies, parents and the planet, CuteyBaby "One and Done!" Modern Cloth Diaper Starter Kit—Girl, 5 pages, (Customer Review, May 22, 2010) biodegradablediapers.info.

Derwent abstract and Figure of CA 2024375A, publication date Mar. 1, 1992.

FuzziBunz, A better diaper for a better planet, Newsletter, FuzziBunz Press Releases, 2 pages, (Jul. 10, 2007).

http://fuzzibunz.com/Fuzzi-Bunz-Colors.htm, 2 pages, accessed and printed Sep. 8, 2006.

http://getantsy.com/Antsy-Pants-Are.html, Antsy Pants™ Pull-Up Cloth Diapers, Optimized for Potty Training, 2009-2011, 6 pages, accessed and printed Sep. 21, 2011.

http://hydrology-tubarc.blogspot.com/32 pages, accessed Sep. 15, 2008.

http://ip-know-how-tubarc.blogspot.com/, 8 pages, accessed Sep. 15, 2008.

http://tubarc.blogspot.com/, 206 pages, accessed Sep. 15, 2008.

http://web.archive.org/web/20041010045134/www.changingbabies.com/anatomyof-adiaper.html, accessed Apr. 27, 2007, 17 pages.

http://www.cottonbabies.com/index.php, 7 pages, accessed on Aug. 24, 2006.

http://www.diapersite.com/baby_diapers_specs.htrn, 4 pages, accessed Apr. 23, 2008.

http://www.diapersite.com/images/diaperspecs/velcro.htm, 1 page, accessed Apr. 23, 2008.

http://www.gro-via.com/aiotutorial.html, 2011 The Natural Baby Company, 4 pages, accessed and printed Sep. 21, 2011.

http://www.tinytush.com/, 6 pages, accessed and printed Sep. 8, 2006.

http://www.wonderworksbabyco.com/products.htm, 5 pages, accessed and printed Sep. 8, 2006.

http:www.aplix.com/en/layout/set/print/content/search, accessed Apr. 27, 2007, 3 pages.

https://www.gro-via.com/mychoice-trainer.html, 2011 The Natural Baby Company, 5 pages, accessed and printed Sep. 21, 2011.

Definition of "Waterproof", Webster's Third New International Dictionary, unabridged, 1993, 1 page.

US Patent Office Non-final Office action dated Jun. 6, 2012 issued in U.S. Appl. No. 12/632,315, which also claims priority to the same U.S. Appl. No. 11/518,587 (now U.S. 7,629,501 issued Dec. 8, 2009) as the instant application; 28 pgs.

US Patent Office Final Office action dated Jan. 9, 2013 issued in U.S. Appl. No. 12/632,315, which also claims priority to the same U.S. Appl. No. 11/518,587 (now U.S. 7,629,501 issued Dec. 8, 2009) as the instant application; 14 pgs.

US Patent Office Final Office action dated Jul. 16, 2013 issued in U.S. Appl. No. 12/632,315, which also claims priority to the same U.S. Appl. No. 11/518,587 (now U.S. 7,629,501 issued Dec. 8, 2009) as the instant application, 14 pgs.

Canadian Office Action dated Mar. 25, 2014 for Canadian application No. 2,844,249 which names the same inventors but is not related through a priority claim; 3 pages.

\* cited by examiner

REUSABLE DIAPERS HAVING SEAM ALLOWANCES

CROSS-REFERENCE TO RELATED APPLICATION

This application is a continuation of U.S. patent application Ser. No. 12/059,844 filed Mar. 31, 2008, which, in turn, is a continuation-in-part of U.S. patent application Ser. No. 11/518,587 filed Sep. 8, 2006 (now U.S. Pat. No. 7,629,501 issued Dec. 8, 2009), the entire disclosures of which are incorporated herein by reference.

FIELD

The present disclosure relates generally to reusable diapers.

BACKGROUND

The statements in this background section merely provide background information related to the present disclosure and may not constitute prior art.

Absorbent articles, such as disposable diapers, training pants, or incontinence pads, generally have an absorbent core intended for single use only. Once the absorbent core component is saturated with bodily discharges, such as urine, the entire absorbent article is usually discarded. Oftentimes, parts of a disposable diaper or training pants could be reused. But with the unitary construction, they are nevertheless discarded along with the saturated absorbent cores. In addition to the added cost and waste associated with discarding such products, it is often inconvenient to acquire and store quantities of such disposable absorbent articles.

SUMMARY

According to various aspects, exemplary embodiments are provided of reusable diapers. In one exemplary embodiment, a reusable diaper generally includes at least one inner layer configured to wick moisture and at least one outer layer configured to be substantially impervious to liquids. A waist portion is generally defined by the at least one inner layer and the at least one outer layer. The waist portion includes a corner region which can be used to secure the reusable diaper in a desired position. The corner region includes a first layer and a second layer which are coupled together to define an interior portion of the corner region. The first layer is further coupled to the at least one inner layer and the second layer is further coupled to the at least one outer layer. The reusable diaper also includes a first seam allowance which is defined generally by the first layer of the corner region and the at least one inner layer. The first seam allowance is positioned generally within the interior portion of the corner region and extends generally away from the at least one inner layer. The reusable diaper also includes a second seam allowance which is defined generally by the second layer of the corner region and the at least one outer layer. The second seam allowance is positioned generally within the interior portion of the corner region and extends generally away from the at least one outer layer. The positioning of the first and second seam allowances generally helps to inhibit wicking of liquid through the seam allowances and into the corner region.

In another exemplary embodiment, a reusable diaper generally includes a waist portion having at least one resiliently stretchable corner region for use in securing the reusable diaper in a desired position. The at least one resiliently stretchable corner region is substantially impervious to liquids.

In another exemplary embodiment, a reusable diaper generally includes at least one inner layer configured to wick moisture and at least one outer layer configured to be substantially impervious to liquids. At least one pocket is defined generally by a space between the at least one inner layer and the at least one outer layer. The at least one pocket is configured to receive at least one liquid-absorbent insert therein. And the at least one inner layer of the reusable diaper includes at least one fluid-resistant region for resisting wicking of moisture past the fluid-resistant region.

In another exemplary embodiment, a reusable diaper generally includes at least one inner layer configured to wick moisture and at least one outer layer configured to be substantially impervious to liquids. At least one pocket is defined generally by a space between the at least one inner layer and the at least one outer layer, and is configured to receive at least one liquid-absorbent insert therein. A waist portion is generally defined by the at least one inner layer and the at least one outer layer. The waist portion includes at least one resiliently stretchable corner region for use in securing the reusable diaper in a desired position. The resiliently stretchable corner region includes a first layer and a second layer coupled together so as to define an interior portion of the corner region. The first layer is further coupled to the at least one inner layer, and the second layer is further coupled to the at least one outer layer. A first seam allowance is defined by the first layer of the corner region and the at least one inner layer. The first seam allowance is positioned generally within the interior portion of the corner region and extends generally away from the at least one pocket. A second seam allowance is defined by the second layer of the corner region and the at least one outer layer. The second seam allowance is positioned generally within the interior portion of the corner region and extends generally away from the at least one pocket. The at least one inner layer includes at least one fluid-resistant region for resisting wicking of moisture past the fluid-resistant region. And the at least one resiliently stretchable corner region is substantially impervious to liquids. Further, the positioning of the first and second seam allowances helps inhibit wicking of liquid from the at least one fluid-absorbent insert received within the at least one pocket through the seam allowances to the resiliently stretchable corner region.

Further aspects and features of the present disclosure will become apparent from the detailed description provided hereinafter. In addition, any one or more aspects of the present disclosure may be implemented individually or in any combination with any one or more of the other aspects of the present disclosure. It should be understood that the detailed description and specific examples, while indicating exemplary embodiments of the present disclosure, are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
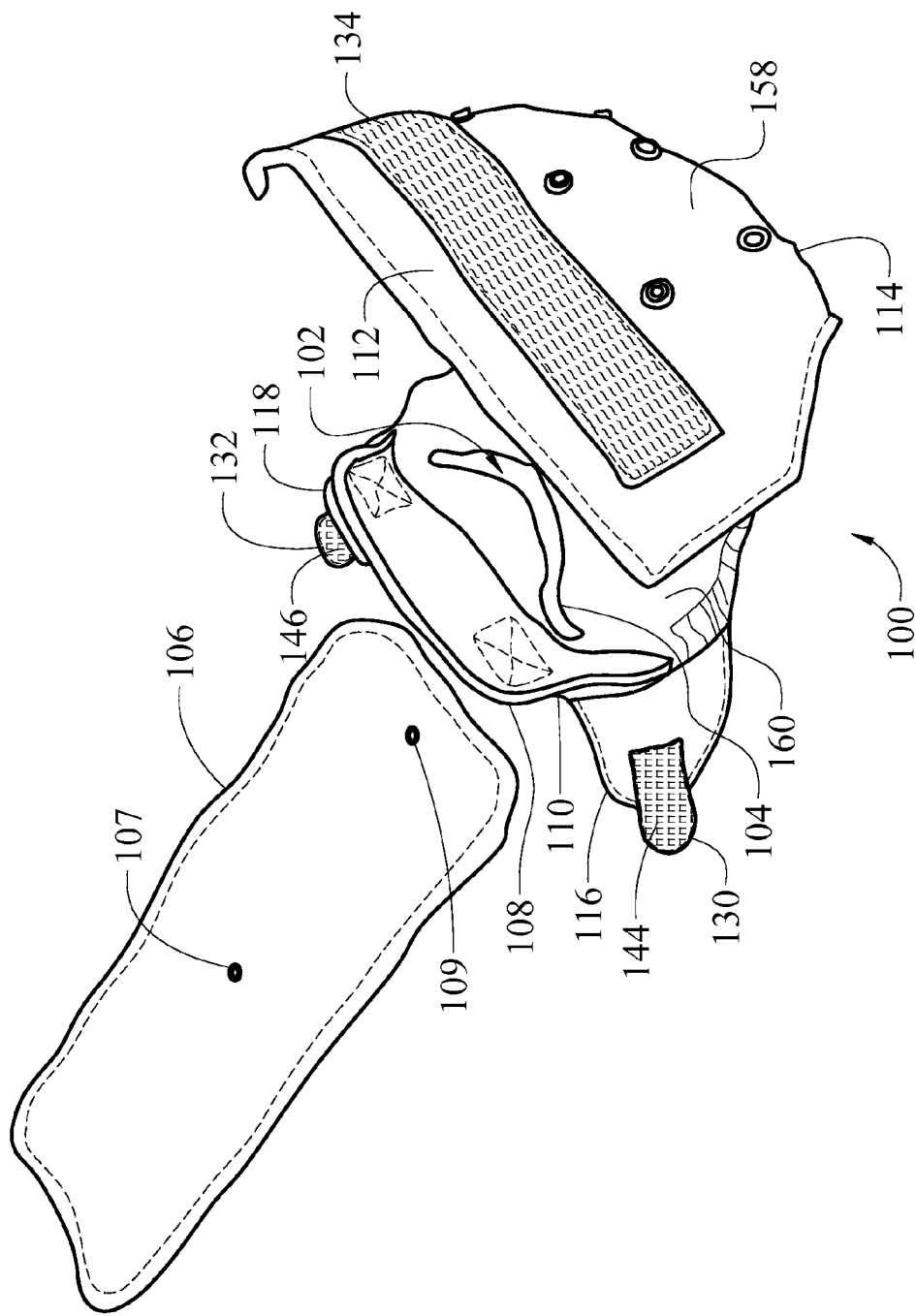
FIG. 1 is an exploded perspective view of a reusable diaper having a pocket opening and a flap according to exemplary embodiments, wherein the flap is shown in an opened configuration in which the opening into the pocket is exposed to allow a liquid-absorbent insert to be positioned within the pocket.

The following description is merely exemplary in nature and is in no way intended to limit the present disclosure, application, or uses.

According to various aspects, exemplary embodiments are provided of reusable diapers. In one exemplary embodiment, a reusable diaper generally includes an inner layer configured to wick moisture from the diaper wearer's body and an outer layer configured to be substantially liquid-impervious. At least one pocket is defined generally by a space between the inner and outer layers. The at least one pocket is configured to receive at least one liquid-absorbent insert therein. The diaper also includes at least one slit in the inner layer that provides access into the space between the inner and outer layers defining the at least one pocket. At least one flap is provided that is positionable in an open configuration or a closed position. When the at least one flap is in the open configuration, the at least one slit is exposed and allows access into the at least one pocket. In the closed configuration, however, the at least one flap substantially covers the at least one slit and inhibits contact between the diaper wearer and at least one liquid-absorbent insert positioned within the at least one pocket. When closed, the at least one flap may also inhibit the inadvertent or accidental removal of the at least one liquid-absorbent insert from the at least one pocket.

In another exemplary embodiment, a reusable diaper generally includes first and second waist portions. The first waist portion includes corner regions that are releasably attachable to the second waist portion. The corner regions may be resiliently stretchable to permit at least some adjustability to the diaper's functional waist size as defined by the first and second waist portions when the first waist portion is releasably attached to the second waist portion.

In another exemplary embodiment, a reusable diaper generally includes a forward portion, a rearward portion, and a crotch portion. The reusable diaper further includes at least a three-by-three array of snap members along the forward portion that allows selective adjustment to the diaper's functional rise or crotch length. The array includes at least a first row of at least three spaced-apart snap members (e.g., plastic male snap members, plastic female snap members, combinations thereof, etc.). The snaps in the first row are vertically spaced from and aligned with corresponding snap members (e.g., plastic female snap members, plastic male snap members, combinations thereof, etc.) in at least two other rows of the array. For example, snap members in a first or top row can be snapped together with the corresponding snap members in the second or middle row to decrease the diaper's functional rise or crotch length. Or, for example, the snap members of the top row can be snapped together with the corresponding snap members in a third or bottom row to even further decrease the diaper's functional rise or crotch length. Advantageously, having at least three columns of snaps may provide a more snug and precise fit to the diaper wearer, for example, by reducing the extent to which the crotch portion hangs down below the wearer. For example, the three-by-three arrangement can eliminate or at least reduce the bulge in the middle front of the diaper that typically occurs when there are only two columns of snaps due to the fabric bulging out between the two snaps. The three-by-three snap arrangement may enable the diaper to be more of a one-size fits all cloth diaper. Alternative embodiments may include more or less than three rows of snaps, more or less than three columns of snaps, and/or different connector members besides snaps.

In some embodiments, a reusable diaper may include at least one inner liner or layer. The at least one inner layer can be configured to wick moisture from the diaper wearer's body generally towards the at least one liquid-absorbent insert within the at least one pocket. The reusable diaper may further comprise at least one outer layer or liner along at least an outer portion of the reusable diaper. The at least one outer layer can be substantially liquid-impervious to thereby resist wicking of moisture through the at least one outer layer. In some preferred embodiments, the outer layer is formed of polyester, and the inner layer is formed of suede cloth. Alternatively, other suitable materials may be used for the inner and/or outer layers.

In some embodiments, there may be provided a plurality of replacement liquid-absorbent inserts. In such embodiments, an existing liquid-absorbent insert may be removed from a pocket after the insert has become saturated. One of the replacement inserts can be positioned within the pocket after the diaper has been washed or laundered.

Other embodiments of a reusable diaper may include a first waist portion having corner regions with tabs releasably attachable to a second waist portion. The corner regions may be resiliently stretchable to permit some adjustability to the functional waist size of the reusable diaper as defined by the first and second waist portions. In some embodiments, the corner regions may be formed from 95% polyester and 5% Lycra. Alternatively, the corner regions may be formed using other suitable materials. The tabs may also be releasably attachable to an interior portion of the diaper (e.g., to a back side of a flap, etc.) for retaining the corner regions and tabs within the interior of the reusable diaper. A wide range of attachment means may be used for releasably attaching the tabs to the second waist region and/or to an interior portion of the diaper, such as hook-and-loop fasteners, snaps, buttons, adhesives, combinations thereof, etc.

Referring now to FIGS. 1 through 6, there is shown an exemplary embodiment of a reusable diaper 100 embodying one or more aspects of the present disclosure. As shown, the reusable diaper 100 includes a first waist portion or region 110, a second waist portion or region 112, and a crotch portion or region 114 disposed generally between the first and second waist portions 110, 112. The first waist portion 110 includes corner regions 116 and 118. The second waist portion 112 includes corner regions 120 and 122.

Figure 2:
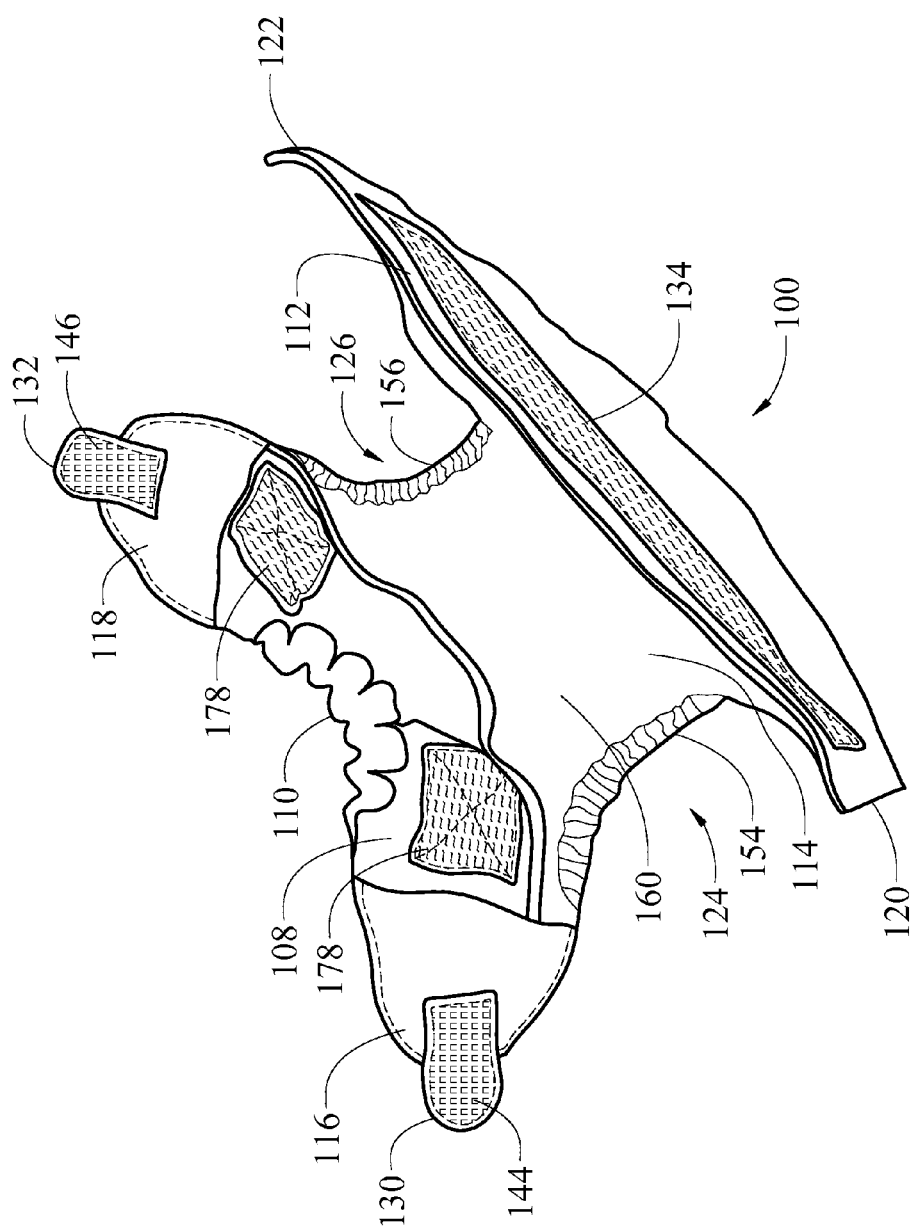
FIG. 2 is a perspective view of the reusable diaper shown in FIG. 1, wherein the flap is shown in the closed configuration in which the flap substantially covers the opening into the pocket and inhibits contact between the diaper wearer and the liquid-absorbent insert positioned within the pocket.
Figure 3:
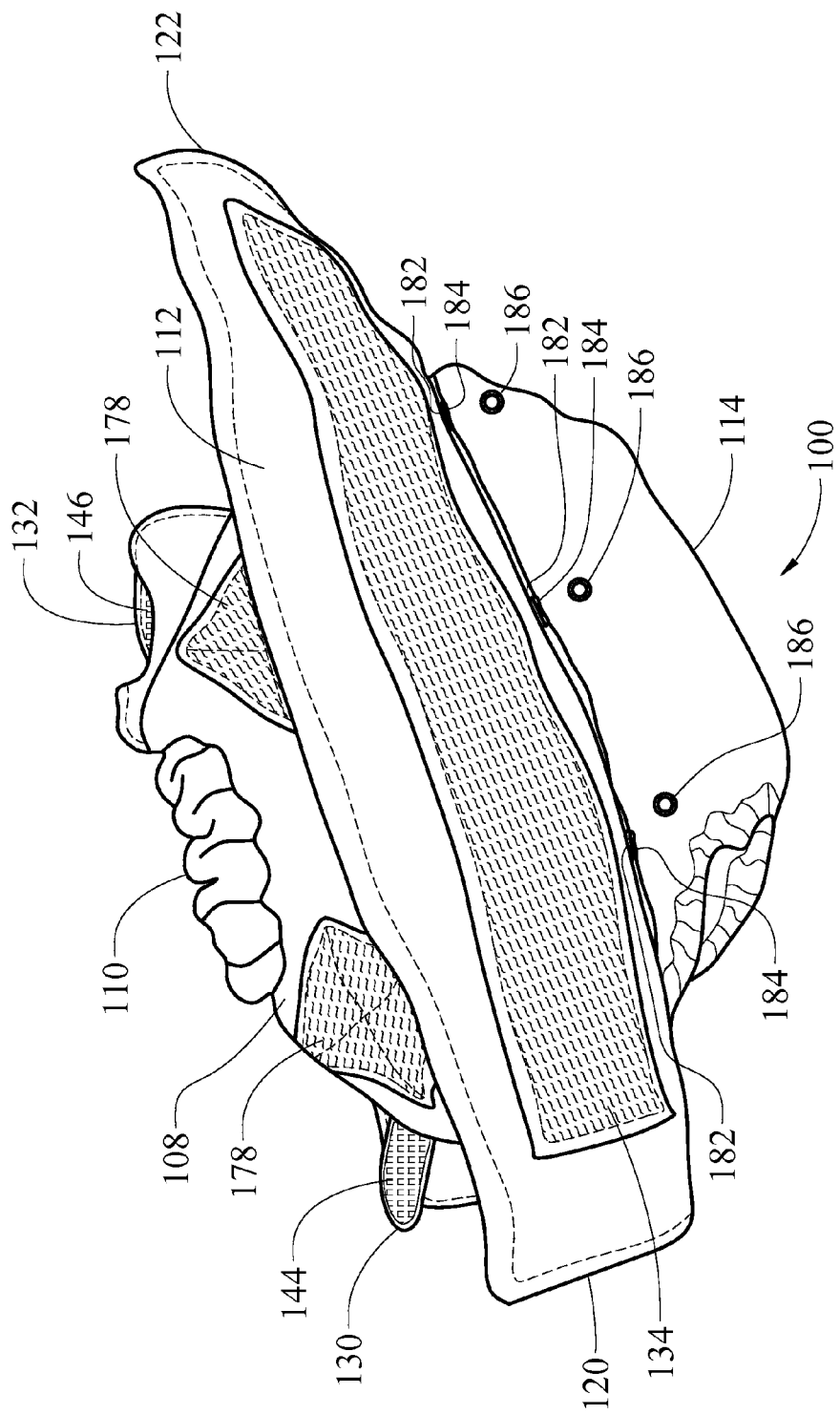
FIG. 3 is a front perspective view of the reusable diaper shown in FIGS. 1 and 2, wherein the top row of snap members have been snapped into the corresponding snap members in the middle row thereby reducing the diaper's functional rise or crotch length.
Figure 4:
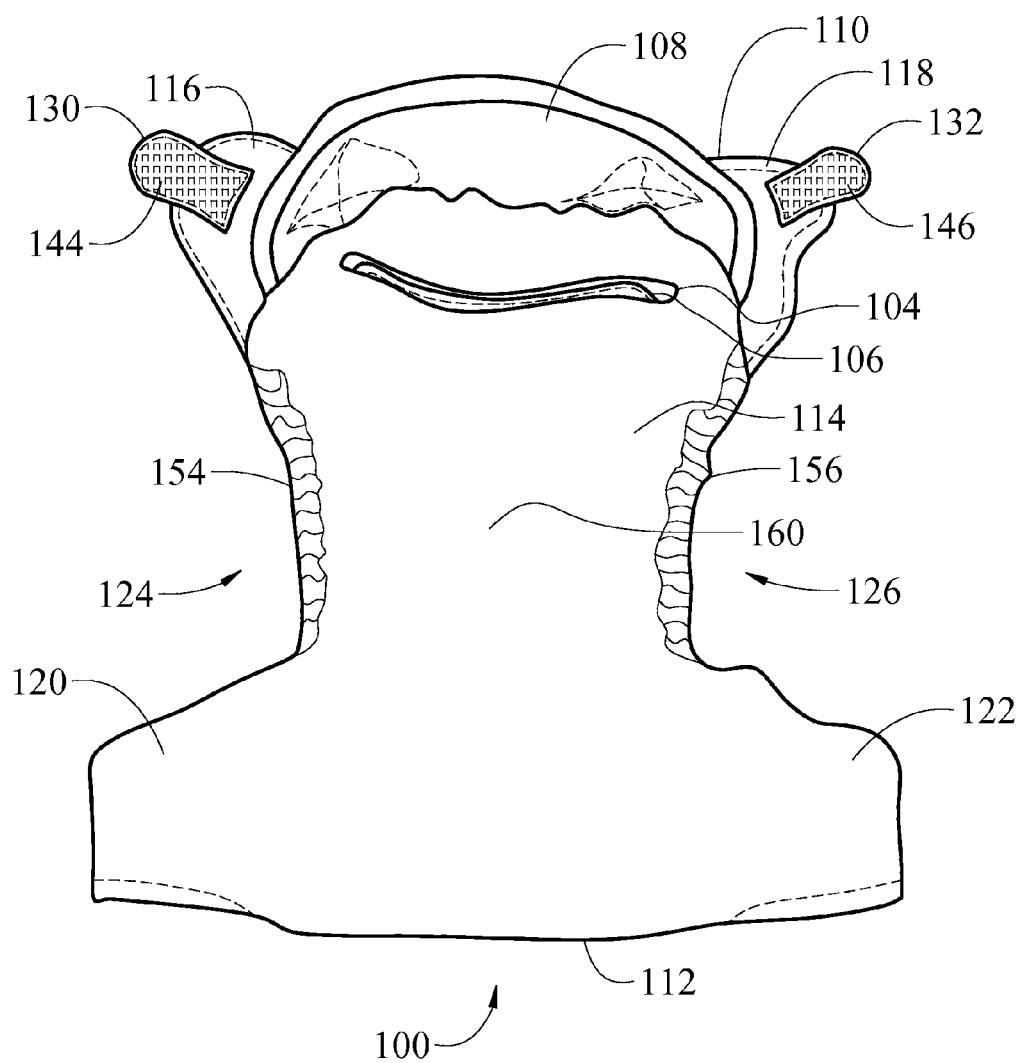
FIG. 4 is an inner view of the reusable diaper shown in FIGS. 1 through 3.

As shown in FIG. 2, the contours of the corner regions 116, 118, 120, 122 and crotch portion 114 cooperatively define leg openings 124 and 126. For example, leg opening 124 is cooperatively defined by the curve extending from the first waist portion's corner region 116 along the crotch portion 114 to the second waist portion's corner region 120. In addition, the other leg opening 126 is defined by the curve extending from the first waist portion's corner region 118 along the crotch portion 114 to the second waist portion's corner region 122. In this illustrated embodiment, the leg openings 124 and 126 may further comprise elastic disposed adjacent the periphery of the leg openings 124 and 126, for example, to help draw and hold the diaper 100 against the wearer's legs.

Figure 5:
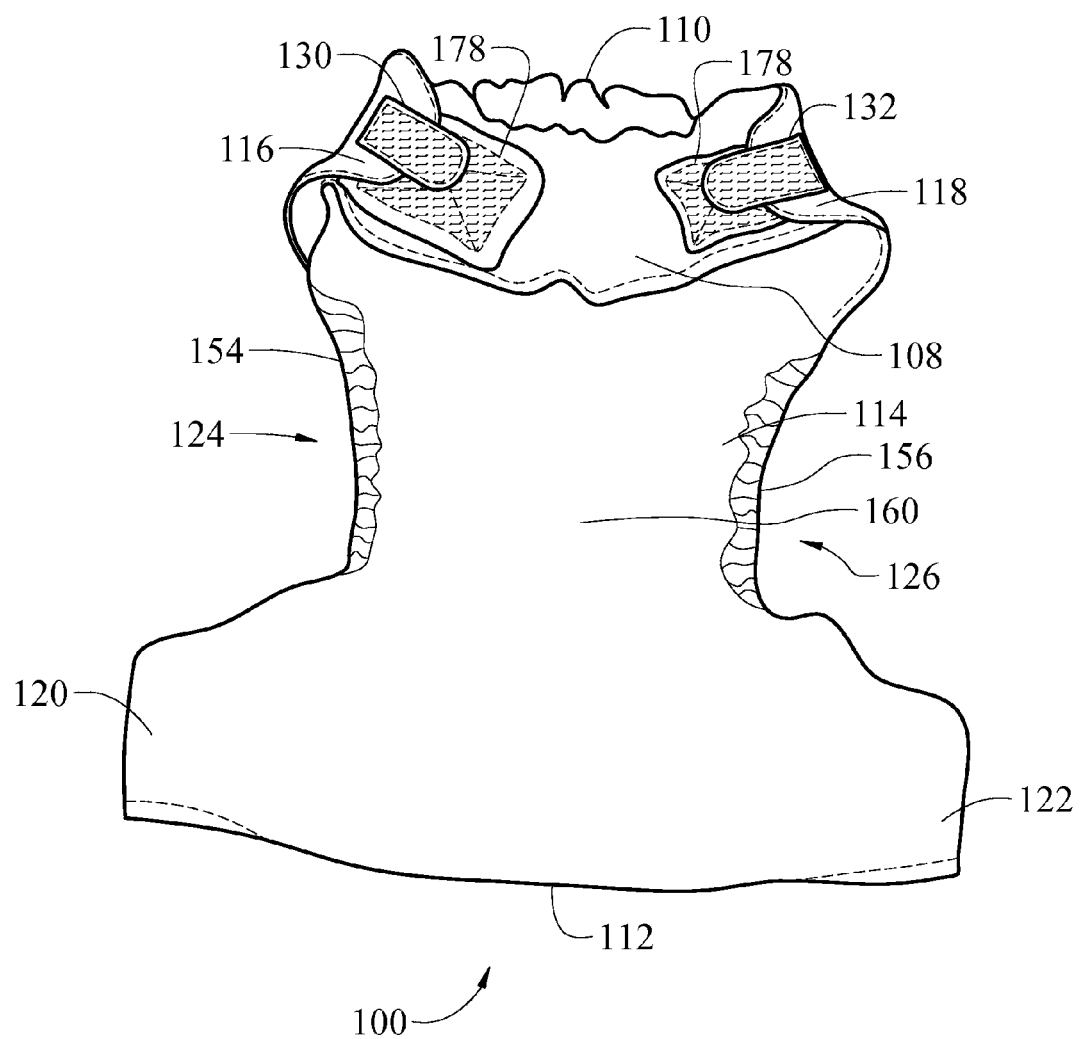
FIG. 5 is an inner view of the reusable diaper shown in FIG. 4, wherein tabs have been releasably attached to the flap with hook-and-loop fasteners.

With continued reference to FIG. 1, the reusable diaper 100 includes a pocket 102 defined generally by the space between the diaper's outer layer 158 and inner layer 160. The diaper 100 also includes an opening or slit 104 in the inner layer 160 that allows access into the pocket 102. The reusable diaper 100 further includes a flap 108 positionable in either an open configuration (FIGS. 1 and 4) or a closed configuration (FIGS. 2 and 5).

When the flap 108 is in the open configuration, the slit 104 is exposed and allows access into the pocket 102. In the closed configuration, however, the flap 108 substantially covers the slit 104 and inhibits contact between the skin or clothes of the diaper wearer and the liquid-absorbent insert 106 positioned within the pocket 102. Additionally, closing the flap 108 may also inhibit the inadvertent or accidental removal of the insert 106 from the pocket 102. In alternative embodiments, a suitable attachment means may be employed for releasably retaining the flap in the closed position, such as hook-and-loop fasteners, snaps, adhesives, buttons, clasps, magnets, combinations thereof, etc.

The flap 108 may be formed from a wide variety of materials. In some preferred embodiments, the flap 108 is formed from one or more fabric materials, such as suede cloth, etc. In such embodiments, the flap 108 and the inner layer 160 may be formed from the same materials. Alternatively, the flap 108 and inner layer 160 may be formed from different materials.

The flap 108 may be attached to the reusable diaper 100 using a wide variety of attachment methods, such as stitching, sewing, adhesive attachment, integrally formed, etc. In some preferred embodiments, the flap 108 is attached to the inner layer 160 along the diaper's rear portion by stitching or sewing. In such embodiments, the flap 108 and opening 104 into the pocket 102 are not readily accessible by the diaper wearer.

As shown in FIG. 1, a liquid-absorbent insert 106 can be received within the pocket 102 via the slit 104. The insert 106 is preferably configured to absorb and store liquids therein. The insert 106 may comprise one or more of microfibers, hemp, hydrocolloid materials, or any other suitable material configured to absorb and store liquids therein.

In this particular embodiment, the insert 106 is shown with snap members 107 and 109. These snap members 107, 109 can be snapped together or unsnapped to thereby allow selective adjustment to the length of the insert 106. For example, the snap member 107 can be snapped together with the snap member 109 to decrease the insert's length. Or, for example, the snap members 107 and 109 can be unsnapped to increase the insert's length. This lengthwise adjustability can allow the insert 106 to more precisely fit within the pocket 102, for example, when the functional rise or crotch length of the diaper is changed by way of the array of snaps 180 (as described in more detail below). Alternative embodiments may include an insert having more or less snaps and/or snaps in other arrangements to accommodate lengthwise adjustability to the insert. Further embodiments may include an insert having a wide range of other suitable fastening systems besides snaps, such as adhesives, buttons, clasps, Velcro® hook and loop closures, magnets, elastic straps, adjustable straps, combinations thereof, etc.

In the illustrated embodiment, the pocket 104 is defined generally by the space between the diaper's outer layer 158 and inner layer 160. The pocket's periphery or perimeter is defined to extend generally from about the first waist portion 110 along the first and second edge portions 154, 156 of the crotch region 114 to about the second waist portion 112. Stitching (or other suitable means) may be used to secure the perimeter or periphery of the pocket 102. For example, the illustrated embodiment has the pocket periphery formed generally by the same stitching used to attach the outer and inner layers 160, 158 to each other.

A wide range of suitable materials may be used for the inner and outer layers 160, 158. The inner layer 160 is preferably configured to wick moisture generally away from the diaper wearer towards the insert 106 within the pocket 102. The outer layer 158 is preferably configured to be substantially liquid-impervious to thereby resist wicking of moisture through the outer layer 158. In one preferred embodiment, the outer layer 158 is formed of polyester, and the inner layer 160 is formed of suede cloth. Alternatively, other suitable materials may be used for the inner liner and/or outer layers 160, 158.

Accordingly, the reusable diaper 100 may be put on a wearer with the inner layer 160 positioned against the skin of the wearer. In which case, the inner layer 160 can wick moisture (e.g., bodily discharge, urine, sweat, etc.) through the inner layer 160 to the liquid-absorbent insert 106 within the pocket 102. When the insert 106 has become saturated, the insert 106 may be removed and then washed or laundered along with or separately from the diaper 100. After the diaper 100 and insert 106 have been satisfactorily washed and dried, the insert 106 may be repositioned within the pocket 102 of the diaper 100. At which point, the diaper 100 may be reused.

In some preferred embodiments, the first waist portion's corner regions 116 and 118 are resiliently stretchable. This feature allows at least some adjustability to the diaper's functional waist size as defined by the first and second waist portions 110 and 112 when the first waist portion 110 is releasably attached to the second waist portion 112. In some embodiments, the corner regions may be formed from 95% polyester and 5% Lycra. Alternatively, the corner regions may be formed using other suitable materials.

With reference to FIG. 2, the reusable diaper 100 includes tabs 130, 132 associated with the first waist portion 110. In addition to stretchable corner regions, some embodiments also configure the tabs 130, 132 to be resiliently elastic or stretchable. This, in turn, can permit further adjustability to the diaper's functional waist size. In yet other embodiments, only the tabs 130 and 132 are resiliently elastic or stretchable. In further embodiments, however, the tabs 130, 132 may be essentially inelastic or stretchable.

The tabs 130, 132 may include respective hook-and-loop fastener portions 144, 146, which, in turn, are releasably attachable to corresponding hook-and-loop fastener portions of the second waist portion 112. As shown in FIG. 2, the second waist portion 112 includes an elongate strip 134 having hook-and-loop fastener portions extending along the length thereof. Accordingly, the hook-and-loop fastener portions 144, 146 of the tabs 130, 132, respectively, can be releasably attachable at different locations along the elongate strip 134, which allows the first waist portion 110 to be adjustably secured to the second waist portion 112 when positioned around a wearer of the reusable diaper 100.

Having resiliently elastic or stretchable corner regions 116, 118 (and/or tabs 130, 132 in some embodiments) with the ability to stretch can allow for tailoring of the diaper's functional waist size to the wearer's actual waist size. For example, the diaper's functional waist size may be selectively tailored for the wearer by stretching the corner regions 116, 118, and then releasably attaching the tabs 130, 132 to the elongate strip 134 at particular attachment locations along the length of the elongate strip 134. In this exemplary manner, the diaper's functional waist size can be selectively adjusted, for example, to provide a relatively snug fit about the waist of the wearer (e.g., infant, toddler, adult, etc.), and preferably without being too uncomfortably tight about the wearer's thighs. Alternative embodiments may include other suitable means for allowing selective adjustment to the functional or operational waist size of the reusable diaper. In addition, other suitable fastening systems may also be employed for releasably attaching the diaper's first and second waist portions to each other, such as different hook-and-loop fastener arrangements (e.g., two or more spaced-apart discrete patches along the second waist portion instead of a single elongate strip, etc.), adhesives, snaps, buttons, clasps, Velcro® hook and loop closures, magnets, combinations thereof, etc.

In some embodiments, the tabs 130, 132 may be releasably attachable to an interior portion of the diaper for retaining the corner regions and tabs within the interior of the reusable diaper. As shown in FIG. 2, the tabs 130, 132 include hook-and-loop fastener portions 144, 146 releasably attachable to corresponding hook-and-loop fastener portions 178 of the flap 108. Releasably attaching the tabs 130 and 132 to the flap 108 by way of the hook-and-loop fastener portions 144, 146, 178 (FIG. 5) helps retain the tabs 130 and 132 and corner regions 116 and 118 within an interior of the diaper 100. This, in turn, may help to prevent or at least reduce snagging of the tabs 130, 132 when the reusable diaper 100 is being washed or laundered. Alternatively, a wide range of other attachment means may be used for releasably attaching the tabs 130, 132 to an interior portion of the diaper, such as hook-and-loop fasteners, snaps, buttons, adhesives, combinations thereof, etc.

In some embodiments, the tabs 130, 132 may be releasably attachable to each other. For example, one of the tabs 130 or 132 may have a forward surface with hook-and-loop fasteners that are releasably attachable to hook-and-look fasteners on a rearward surface of the other tab 130 or 132. Alternatively, other suitable fastening means can be employed to implement this feature.

Figure 6:
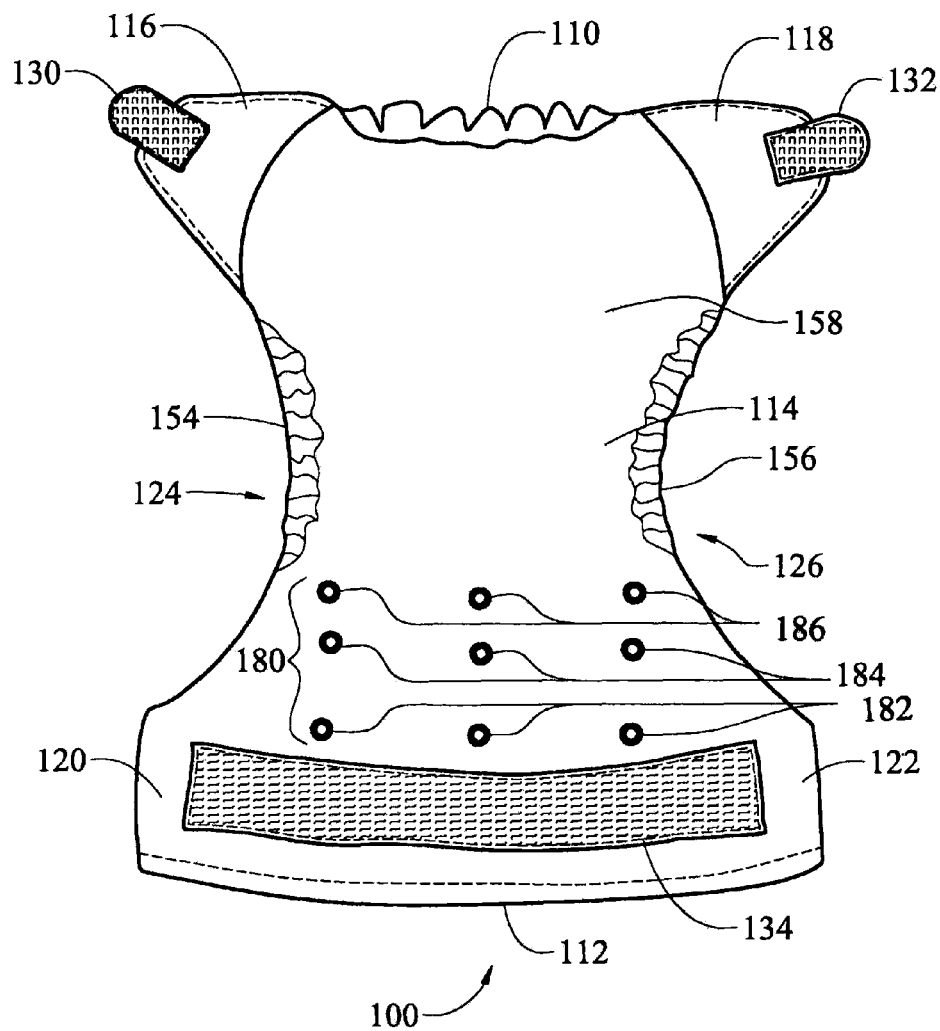
FIG. 6 is an outer view of the reusable diaper shown in FIGS. 1 through 5.

With reference to FIG. 6, the reusable diaper 100 includes snaps that allow for customization or adjustment to the diaper's functional rise or crotch length. This feature may help create an even better or snugger fit to the diaper wearer. For example, the snaps can allow for a reduction in the diaper's functional rise or crotch length so as to reduce the extent to which the crotch portion 114 hangs down below the wearer.

As shown in FIG. 6, the diaper 100 includes a three-by-three array 180 of snap members. The snap members comprising the three-by-three array 180 are horizontally arranged and aligned in the three rows and vertically arranged and aligned in the three columns. Advantageously, having at least three columns may provide a more snug and precise fit to the diaper wearer, for example, by reducing the extent to which the crotch portion hangs down below the wearer. The three-by-three arrangement can eliminate or at least reduce the bulge in the middle front of the diaper that typically occurs when there are only two columns of snaps due to the fabric bulging out between the two snaps. The three-by-three snap arrangement may enable the diaper to be more of a one-size fits all cloth diaper.

In the illustrated embodiment, the first row includes three spaced-apart male snap members 182. The second or middle row includes three spaced-apart female snap members 184. The third row includes three-spaced apart female snap members 186. The male snap members 182 can be snapped together with either the female snap members 184 of the second row, or the female snap members 186 of the third row. For example, the male snap members 182 in the first row can be snapped together with the corresponding female snap members 184 in the second or middle row to decrease the diaper's functional rise or crotch length. To decrease the diaper's functional rise and crotch length to an even greater extent, the male snap members 182 of the first row may instead be snapped together with the corresponding female snap members 186 in the third row. Accordingly, these snap options thus provide three different configurations for the diaper 100. That is, the functional rise or crotch length of the reusable diaper 100 can be changed by selectively choosing whether to engage the male snap members 182 with the female snap members 184 or the female snap members 184, or by simply choosing to do neither.

In some preferred embodiments, the snap members 182, 184, 186 are plastic. Alternatively, the snap members can be formed from other materials, which are preferably relatively lightweight and durable to withstand repeated laundry cycles.

In alternative embodiments, a reusable diaper may include more or less snap options and/or snap members in other arrangements than what is shown in FIG. 6. For example, another embodiment may include two rows of male snap members with only one row of female snap members. As another example embodiment, a diaper may include a row having both male and female snap members. Additional examples include diapers having more or less than three rows of snap members and/or more or less than three columns of snap members. Still further embodiments may include a wide range of other suitable fastening systems besides snaps, such as adhesives, buttons, clasps, Velcro® hook and loop closures, magnets, elastic straps, adjustable straps, combinations thereof, etc.

In some embodiments, a reusable diaper may also include a foldable front portion along the second waist portion. This foldable front portion may be folded down, for example, to help keep the umbilical area of the diaper wearer clean.

Other aspects of the present disclosure relate to methods. In one exemplary embodiment, a method generally includes positioning at least one liquid-absorbent insert through at least one slit or opening into at least one pocket of a reusable diaper. The method may further include closing at least one flap to substantially cover the at least one slit or opening, whereby the at least one flap inhibits contact between the diaper wearer and the at least one liquid-absorbent insert and/or inhibits the inadvertent removal of the at least one liquid-absorbent insert from the at least one pocket.

In some embodiments, the method may include opening the at least one flap to thereby expose the at least one slit or opening and allow access to the at least one pocket. The method may include removing at least one liquid-absorbent insert from the at least one pocket out through the at least one slit or opening. After laundering or washing the diaper, at least one replacement liquid-absorbent insert may be positioned through the at least one slit into the at least one pocket. As another example, a method may include removing the reusable diaper from a wearer before opening the at least one flap, removing the at least one liquid-absorbent insert, washing or laundering the diaper and the liquid-absorbent insert, and positioning the liquid-absorbent insert within the pocket.

In some embodiments, a method may further comprise selectively adjusting a functional waist size of the reusable diaper to a wearer, by stretching corner regions of a first waist portion of the reusable diaper, and then releasably attaching tabs associated with the corner regions to a second waist portion of the reusable diaper. In some preferred embodiments, the tabs may be releasably attached to the second waist portion by using hook-and-loop fasteners. Additional embodiments, however, may alternatively comprise snaps, buttons, adhesives, magnets, combinations thereof, etc.

Figure 7:
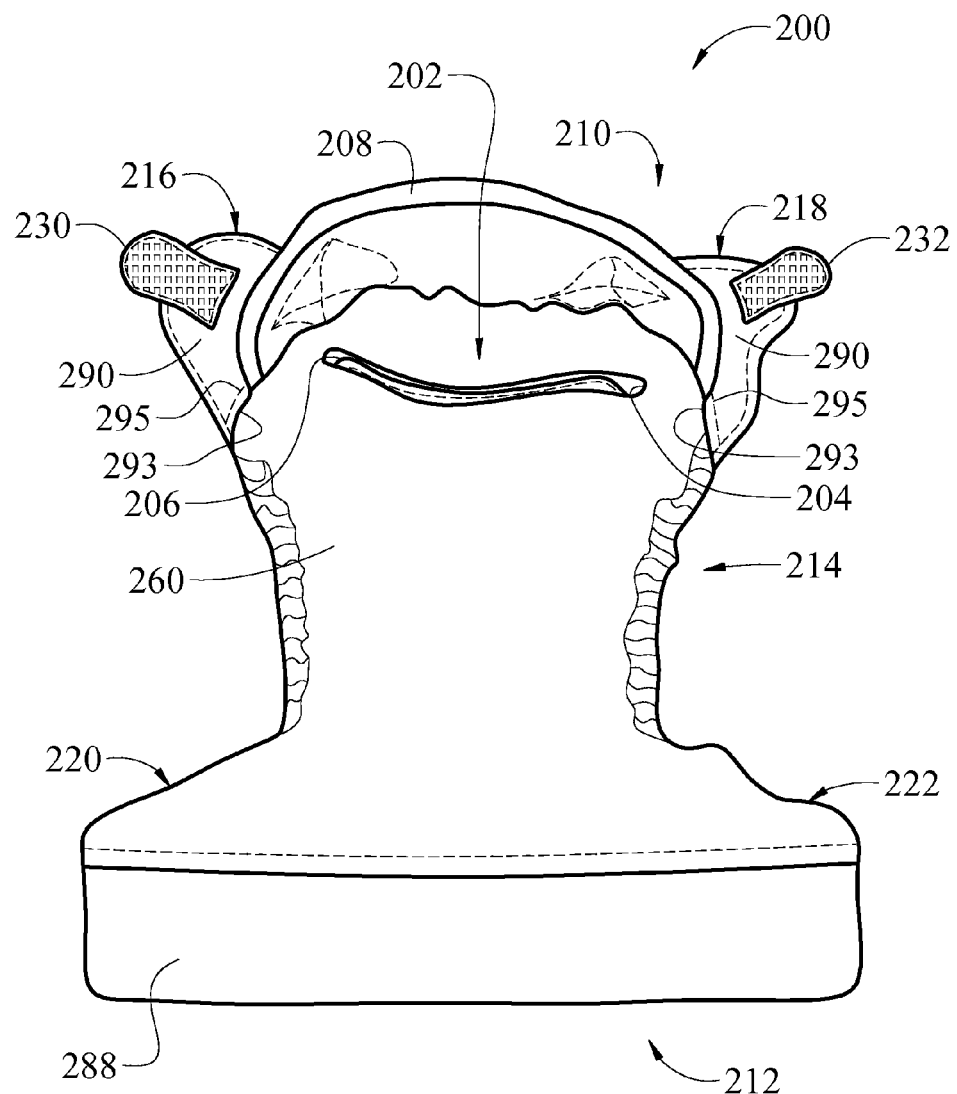
FIG. 7 is an inner view of another exemplary embodiment of a reusable diaper.
Figure 8:
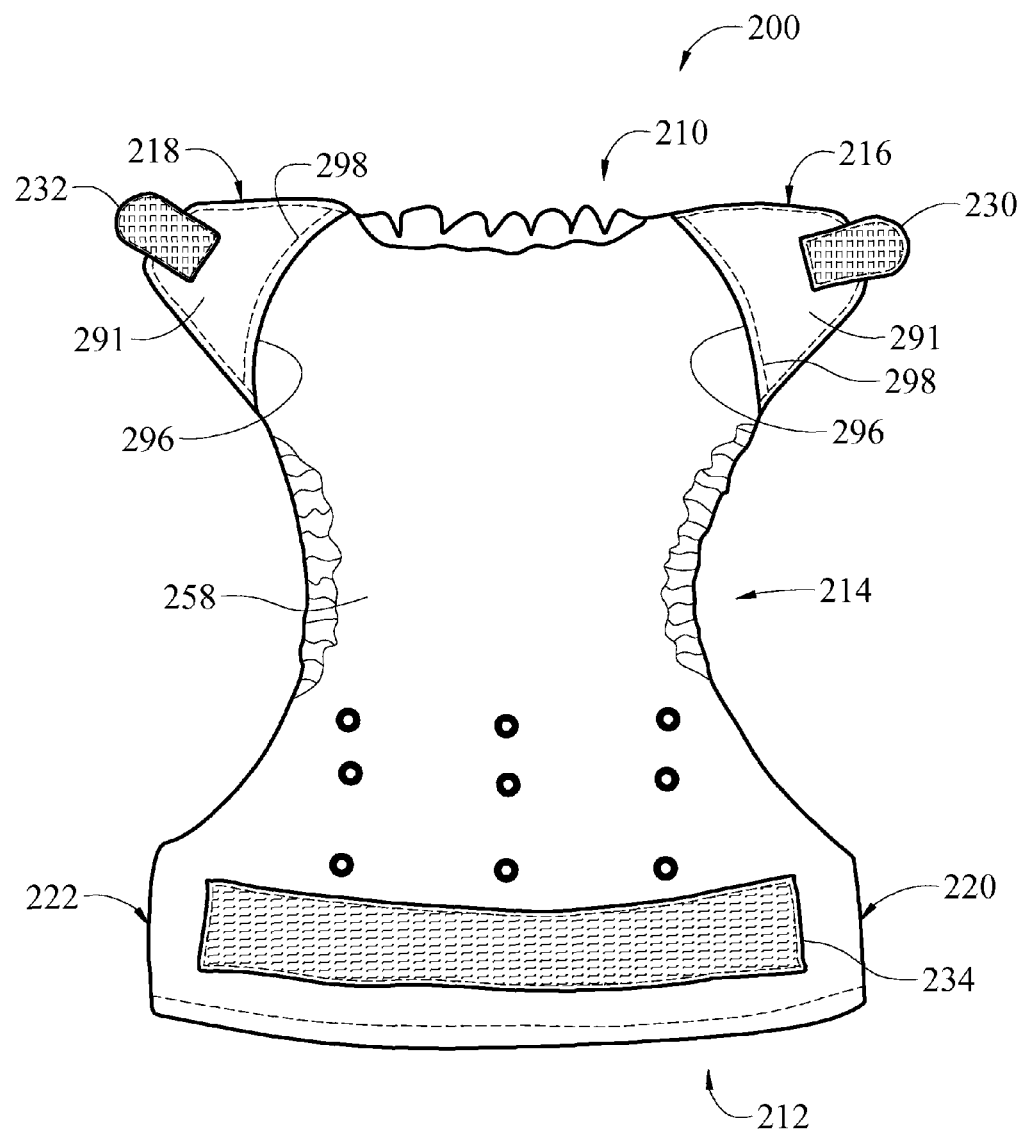
FIG. 8 is an outer view of the reusable diaper of FIG. 7.

FIGS. 7-12 illustrate another exemplary embodiment of a reusable diaper (indicated generally at 200) embodying one or more aspects of the present disclosure. As shown in FIGS. 7 and 8, the reusable diaper 200 generally includes a first waist portion 210 (e.g., a rearward waist portion, etc.), a second waist portion 212 (e.g., a forward waist portion, etc.), and a crotch portion or region 214 disposed generally between the first and second waist portions 210, 212. The first waist portion 210 includes corner regions 216, 218 which are releasably attachable to the second waist portion 212 to secure the reusable diaper 200 in a desired position. More particularly, tabs 230, 232 of the respective corner regions 216, 218 are releasably attachable (e.g., via corresponding hook-and-loop fasteners, etc.) to an elongate strip 234 of the second waist portion 212 (FIG. 8) to secure the diaper in a desired position (e.g., around a wearer, with the wearer generally in contact with an inner layer 260 of the reusable diaper 200, etc.).

The corner regions 216, 218 of the first waist portion 210 may be resiliently stretchable. This feature allows for at least some adjustability of the diaper's functional waist size as defined by the first and second waist portions 210, 212 when the first waist portion 210 is releasably attached to the second waist portion 212. Moreover, the resiliently stretchable corner regions 216, 218 may be substantially impervious to fluids. For example, the resiliently stretchable corner regions 216, 218 may be at least partially coated, treated, etc. with durable water repellant to make them substantially impervious to liquids. Any suitable durable water repellant may be used within the scope of the present disclosure. In other exemplary embodiments, reusable diapers may include resiliently stretchable corner regions having other suitable materials, coatings, etc. applied thereto to make the resiliently stretchable corner regions substantially impervious to liquids.

With continued reference to FIGS. 7 and 8, the reusable diaper 200 also includes an outer layer 258 and the inner layer 260. The outer layer 258 and the inner layer 260 may broadly be viewed as defining at least part of the first and second waist portions 210, 212. The outer layer 258 may be configured to be substantially liquid-impervious to thereby resist wicking of moisture through the outer layer 258, and may be formed, for example, of polyester, nylon, spandex, combinations thereof, etc. The inner layer 260 may be configured to wick moisture generally away, for example, from a diaper wearer, and may be formed, for example, of suede cloth, polyester suede cloth, micro fleece, other forms of fabric designed to wick moisture, combinations thereof, etc. A pocket 202 is defined generally by the space between the diaper's outer layer 258 and inner layer 260. The pocket 202 is configured (e.g., sized, shaped, constructed, etc.) to receive at least one liquid-absorbent insert 206 therein, for example, for help in absorbing and storing liquids (e.g., moisture wicked away from a diaper wearer, etc.). An opening or slit 204 is formed in the inner layer 260 to allow access into the pocket 202, and a flap 208 coupled generally to the first waist portion 210 can be positioned to cover the slit 204 and help retain the liquid-absorbent insert 206 within the pocket 202 as desired.

The reusable diaper 200 may further include one or more fluid-resistant regions that, for example, may help resist wicking of moisture through the diaper 200 past the one or more fluid-resistant regions. In the illustrated reusable diaper 200, the inner layer 260 includes a fluid-resistant region disposed adjacent the second waist portion 212. More particularly in the illustrated reusable diaper 200, and as best shown in FIG. 7, the fluid-resistant region includes a strip 288 coupled (e.g., seamed, stitched, etc.) to both the inner layer 260 and the outer layer 258. Here, the fluid-resistant strip 288 may be viewed as defining at least part of the first waist portion 212. The fluid-resistant strip 288 extends generally across a width of the inner layer 260 substantially from one corner region 220 of the second waist portion 212 to another corner region 222 of the second waist portion 212. This may substantially resist wicking of moisture through the inner layer 260 past the fluid-resistant strip 288. It should be appreciated that a wide range of suitable materials, coatings, laminates, etc. may be used for the fluid-resistant strip 288, including, for example, polyester materials, durable water repellant coatings, etc.

As previously stated, the one or more fluid-resistant regions (e.g., the fluid-resistant strip 288, etc.) of the illustrated reusable diaper 200 may help resist wicking of moisture through the diaper 200 past the one or more fluid-resistant regions. In the illustrated embodiment, for example, the fluid-resistant strip 288 is disposed adjacent the second waist portion 212 and may help prevent wicking of moisture from the reusable diaper 200 (e.g., from the liquid-absorbent insert 206 received within the pocket 202 of the reusable diaper 200, from the inner layer 260 of the reusable diaper 200, etc.) to a shirt, blanket, article of bedding, etc. that may come into contact with a part of the first waist portion 212 (e.g., an inner part of the first waist portion 212, etc.). In other exemplary embodiments, reusable diapers may include inner layers having fluid-resistant regions shaped differently than disclosed herein; having fluid-resistant regions disposed, located, etc. differently than disclosed herein; having fluid-resistant regions with one or more separated parts; etc. For example, in one exemplary embodiment, fluid-resistant regions may be disposed adjacent one or more of waist portions, leg regions, etc. of reusable diapers. In one exemplary embodiment, fluid-resistant regions are disposed adjacent both first and second waist portions of a reusable diaper.

With additional reference now to FIGS. 9-12, the resiliently stretchable corner regions 216, 218 of the first waist portion 210 of the reusable diaper 200 will be described. FIGS. 9-12 illustrate the resiliently stretchable corner region 216, with it understood that a description of the resiliently stretchable corner region 218 would be substantially the same (similar reference numbers are thus used in the figures for corresponding parts of the resiliently stretchable corner regions 216, 218). As shown, the resiliently stretchable corner region 216 includes a first layer 290 and a second layer 291, which are coupled together to define an interior region/portion 292 (FIGS. 11 and 12) of the corner region 216. In the illustrated embodiment, the first layer 290 and the second layer 291 are coupled via stitches. Alternatively, other suitable methods, materials, etc. may be used to couple the first and second layers 290, 291 together to define the interior portion 292 (e.g., epoxy, hot-melt processes, etc.).

Figure 9A:
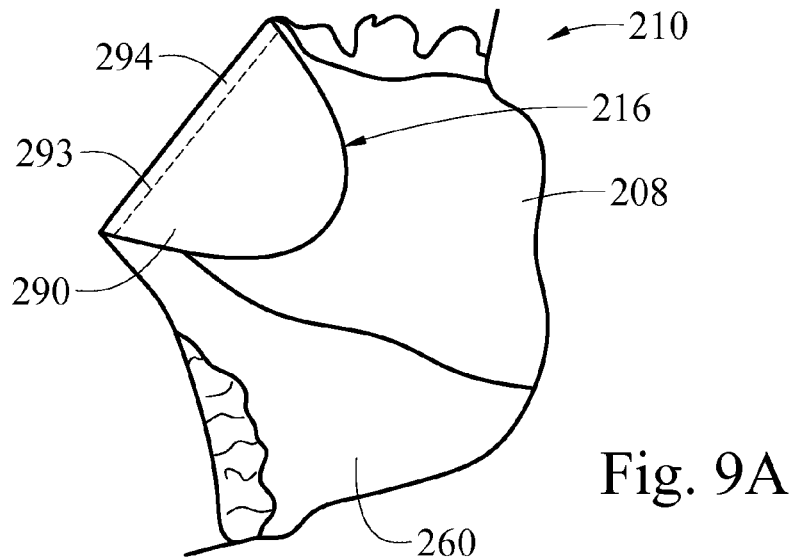
FIG. 9A is a fragmentary inner view of the reusable diaper of FIG. 7 illustrating a first seam allowance formed when stitching a first layer of a corner region to a flap and an inner layer of the reusable diaper.
Figure 9B:
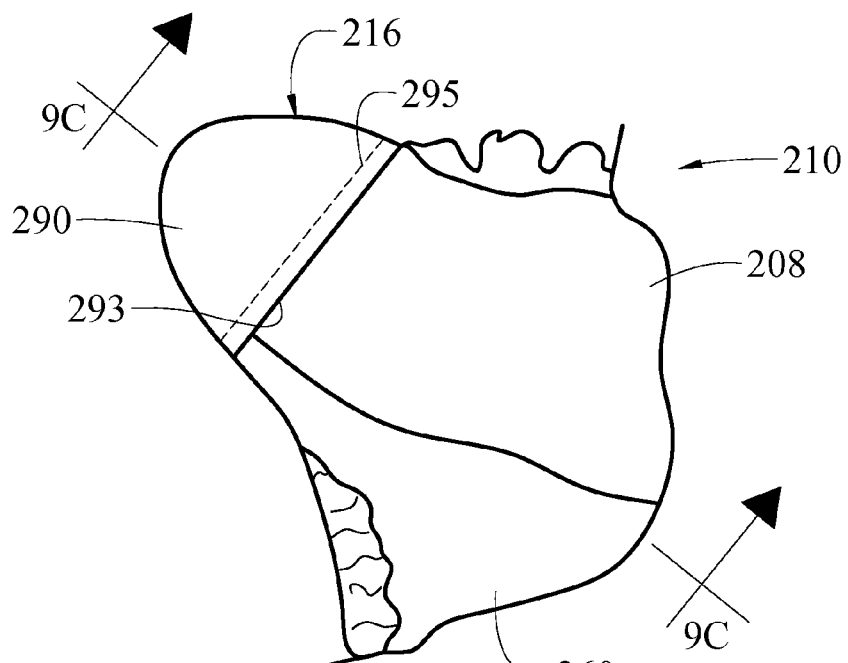
FIG. 9B is a view similar to FIG. 9A illustrating the first seam allowance stitched to the first layer of the corner region.
Figure 9C:
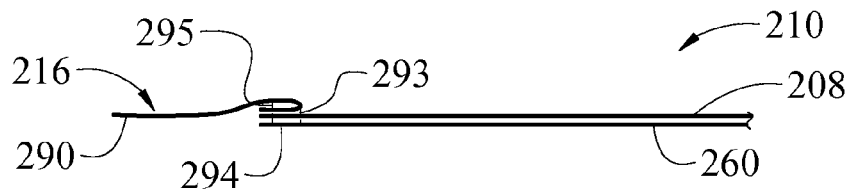
FIG. 9C is a section view taken in a plane including line 9C-9C in FIG. 9B.

As best shown in FIGS. 7 and 9A-9C, the first layer 290 of the illustrated corner region 216 is also coupled to the flap 208 and the inner layer 260 of the reusable diaper 200. To do so, edge margins of the first layer 290, the flap 208, and the inner layer 260 may first be generally aligned such that the first layer 290, the flap 208, and the inner layer 260 are in a generally overlapped position (FIG. 9A). A stitch 293 may then be positioned through the first layer 290, the flap 208, and the inner layer 260 adjacent their generally aligned edge margins to couple them together. This defines a first seam allowance 294 between the stitch 293 and the edge margins of the first layer 290, the flap 208, and the inner layer 260. The first layer 290 may then be folded at the stitch 293 so as to overlap the first seam allowance 294. And a top-stitch 295 may then be positioned through the folded first layer 290 and the first seam allowance 294 (FIGS. 9B and 9C) to couple the first seam allowance 294 to the first layer 290.

Figure 10A:
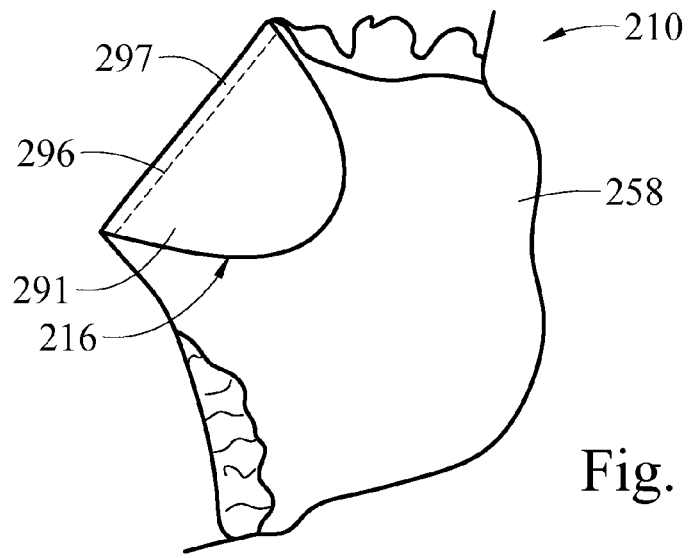
FIG. 10A is a fragmentary outer view of the reusable diaper of FIG. 7 illustrating a second seam allowance formed when stitching a second layer of a corner region to an outer layer of the reusable diaper.
Figure 10B:
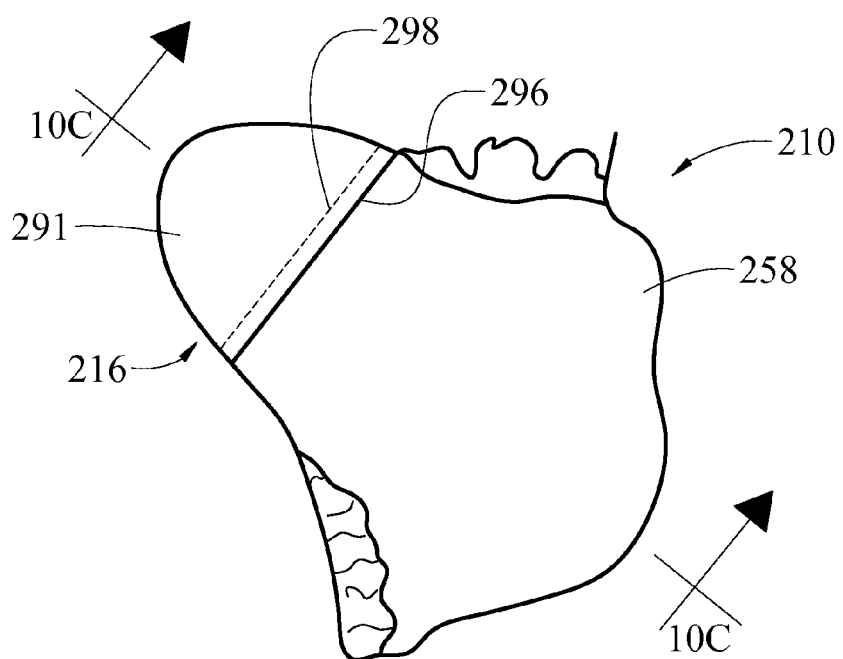
FIG. 10B is a view similar to FIG. 10A illustrating the second seam allowance stitched to the second layer of the corner region.
Figure 10C:
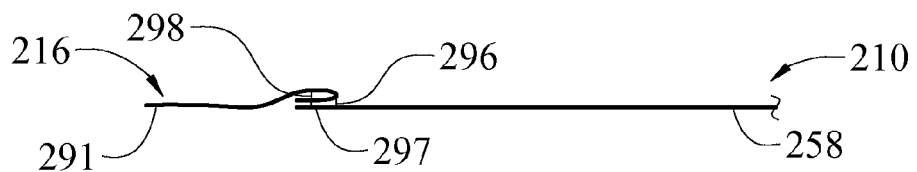
FIG. 10C is a section view taken in a plane including line 10C-10C in FIG. 10B.

As best shown in FIGS. 8 and 10A-10C, the second layer 291 of the corner region 216 is also coupled to the outer layer 258 of the reusable diaper 200. To do so, edge margins of the second layer 291 and the outer layer 258 may first be generally aligned such that the second layer 291 and the outer layer 258 are in a generally overlapped position (FIG. 10A). A stitch 296 may then be positioned through the second layer 291 and the outer layer 258 adjacent their generally aligned edge margins to couple them together. This defines a second seam allowance 297 between the stitch 296 and the edge margins of the second layer 291 and the outer layer 258. The second layer 291 may then be folded at the stitch 296 so as to overlap the second seam allowance 297. And a top-stitch 298 may then be positioned through the folded second layer 291 and the second seam allowance 297 (FIGS. 10B and 10C) to couple the second seam allowance 297 to the second layer 291.

It should be appreciated that at least part of the flap 208, the inner layer 260, and the outer layer 258 may be coupled together before the first and second layers 290, 291 of the corner region 216 are coupled thereto. Alternatively, the first and second layers 290, 291 of the corner region 216 may be coupled to the respective flap 208, inner layer 260, and outer layer 258 of the reusable diaper 200 before the flap 208, inner layer 260, and outer layer 258 are coupled together within the scope of the present disclosure. In addition in other exemplary embodiments, three or more stitches may be used to couple first and second layers of corner regions to respective flaps, inner layers, and outer layers of reusable diapers. In still other exemplary embodiments, reusable diapers may have corner regions coupled thereto other than by stitching (e.g., by epoxy, by hot-melt processes, etc.).

Figure 11:
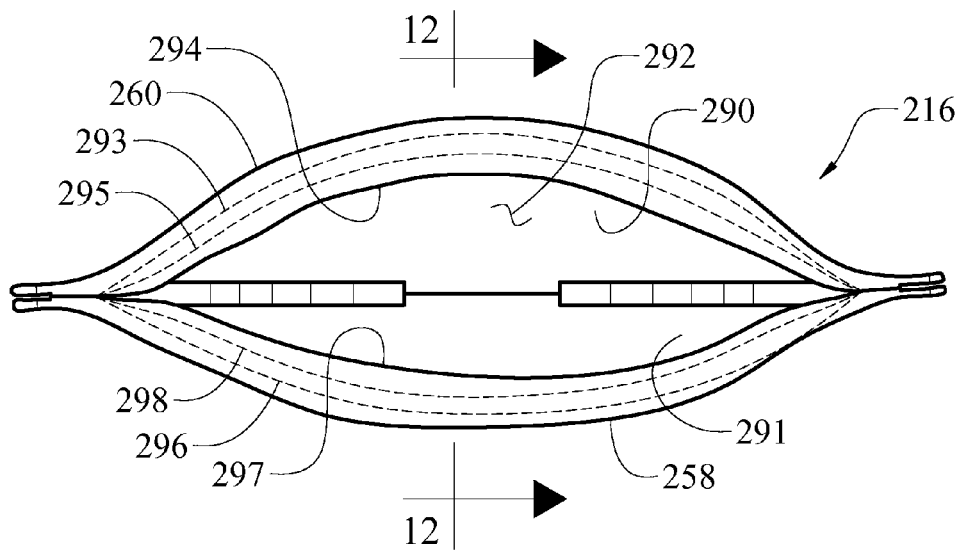
FIG. 11 is a fragmentary view of a corner region of the reusable diaper of FIG. 7 illustrating an interior portion of the corner region with first and second seam allowances disposed generally within the interior portion of the corner region.
Figure 12:
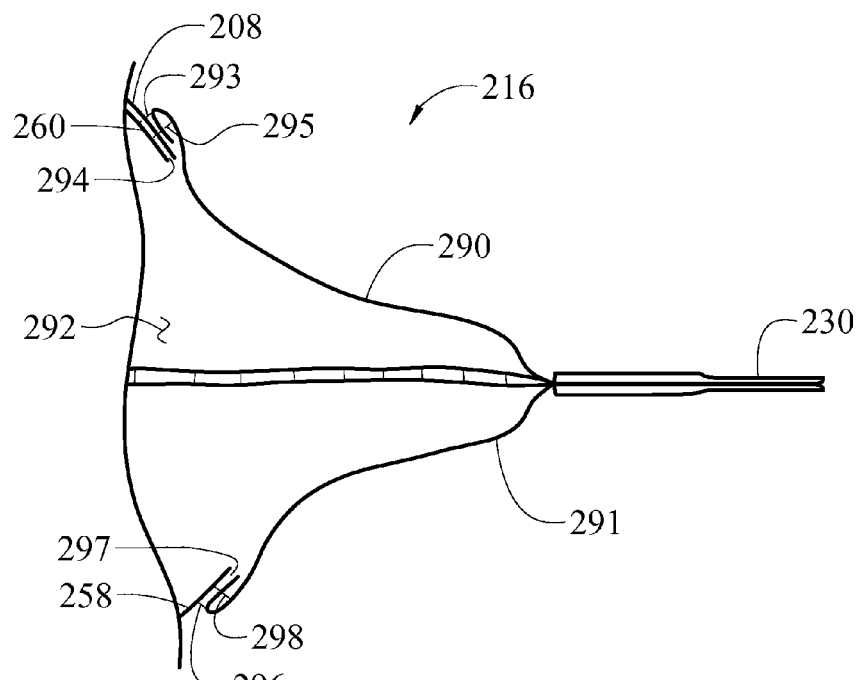
FIG. 12 is a section view taken in a plane including line 12-12 in FIG. 11.

With particular reference now to FIGS. 11 and 12, the first and second seam allowances 294, 297 (when coupled to the respective first and second layers 290, 291 of the corner region 216) are positioned generally within the interior portion 292 of the corner region 216. In this position, the first and second seam allowances 294, 297 each extend generally away from the respective outer layer 258 and inner layer 260 of the reusable diaper 200 (and away from the pocket 202 formed between the outer layer 258 and the inner layer 260). This may help inhibit wicking of liquid through the first and second seam allowances 294, 297 to the corner region 216. For example, in the illustrated reusable diaper 200, moisture moving through the reusable diaper 200 (e.g., through the liquid-absorbent insert 206 received within the pocket 202 formed between the outer and inner layers 258, 260; through the inner layer 260; along the substantially liquid-impervious outer layer 258; etc.) may approach the corner region 216 (as well as the corner region 218) of the first waist portion 210. But the positioning of the first and second seam allowances 294, 297 generally facing away from the moisture transporting regions of the reusable diaper 200 (e.g., the liquid-absorbent insert 206; the inner layer 260; along the substantially liquid-impervious outer layer 258; etc.) may help inhibit the moisture approaching the corner region 216 (as well as the corner region 218) from actually entering and thus wetting the corner region 216. The moisture may not substantially move into contact with the first and/or second seam allowances 294, 297 and thus may not enter the corner regions 216 and/or 218. Thus, the first and second seam allowances 294, 297 are uniquely positioned generally away from the moisture regions of the reusable diaper 200 so as to help inhibit wicking of liquid into the corner regions 216, 218.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom," "side", "inner," "outer," etc. describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order or performance. It is also to be understood that additional or alternative steps may be employed.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A reusable diaper comprising:
    at least one inner layer;
    at least one outer layer; and
    a waist portion having at least one resiliently stretchable corner region for use in securing the reusable diaper in a desired position;
    wherein the at least one resiliently stretchable corner region is substantially impervious to liquids;
    wherein the at least one resiliently stretchable corner region includes a first layer and a second layer coupled together so as to define an interior portion of at least one resiliently stretchable corner region, the first layer being further coupled to the at least one inner layer, and the second layer being further coupled to the at least one outer layer;
    wherein the reusable diaper includes:
        a first seam allowance defined by the first layer of the at least one resiliently stretchable corner region and the at least one inner layer, the first seam allowance being positioned generally within the interior portion of the at least one resiliently stretchable corner region, whereby the first seam allowance helps inhibit wicking of liquid through the first seam allowance and into the at least one resiliently stretchable corner region; and/or
        a second seam allowance defined by the second layer of the at least one resiliently stretchable corner region and the at least one outer layer, the second seam allowance being positioned generally within the interior portion of the at least one resiliently stretchable corner region, whereby the second seam allowance helps inhibit wicking of liquid through the second seam allowance and into the at least one resiliently stretchable corner region.

2. The reusable diaper of claim 1, wherein the at least one resiliently stretchable corner region is at least partially coated with durable water repellent such that the at least one resiliently stretchable corner region is substantially impervious to liquids.

3. The reusable diaper of claim 2, wherein the at least one resiliently stretchable corner region includes at least one tab releasably attachable to the reusable diaper for use in securing the reusable diaper in a desired position.

4. The reusable diaper of claim 3, wherein the waist portion includes two resiliently stretchable corner regions for use in securing the reusable diaper in a desired position, the two resiliently stretchable corner regions each being at least partially coated with durable water repellent such that the two resiliently stretchable corner regions are substantially impervious to liquids.

5. The reusable diaper of claim 4, wherein the waist portion is a first waist portion, the reusable diaper further comprising:
    a second waist portion;
    the two resiliently stretchable corner regions of the first waist portion being releasably attachable to the second waist portion to secure the reusable diaper in a desired position, the resiliently stretchable corner regions permitting at least some adjustability to the functional waist size of the reusable diaper as defined by the first and second waist portions when the first waist portion is releasably attached to the second waist portion.

6. The reusable diaper of claim 2, wherein:
    the at least one inner layer is configured to wick moisture;
    the at least one outer layer is configured to be substantially impervious to liquids; and
    at least one pocket is defined generally by a space between the at least one inner layer and the at least one outer layer, and configured to receive at least one liquid-absorbent insert therein.

7. A reusable diaper comprising:
    at least one inner layer configured to wick moisture;
    at least one outer layer configured to be substantially impervious to liquids;
    at least one pocket defined generally by a space between the at least one inner layer and the at least one outer layer, and configured to receive at least one liquid-absorbent insert therein; and
    a waist portion generally defined by the at least one inner layer and the at least one outer layer, the waist portion having a corner region for use in securing the reusable diaper in a desired position, the corner region including a first layer and a second layer coupled together so as to define an interior portion of the corner region, the first layer being further coupled to the at least one inner layer and the second layer being further coupled to the at least one outer layer;
    wherein the at least one inner layer includes at least one fluid-resistant region for resisting wicking of moisture past the at least one fluid-resistant region;
    wherein the reusable diaper includes:
        a first seam allowance defined by the first layer of the corner region and the at least one inner layer, the first seam allowance being positioned generally within the interior portion of the corner region, whereby the first seam allowance helps inhibit wicking of liquid through the first seam allowance and into the corner region; and/or
        a second seam allowance defined by the second layer of the corner region and the at least one outer layer, the second seam allowance being positioned generally within the interior portion of the corner region, whereby the second seam allowance helps inhibit wicking of liquid through the second seam allowance and into the corner region.

8. The reusable diaper of claim 7, wherein the at least one fluid-resistant region is disposed adjacent the waist portion.

9. The reusable diaper of claim 8, wherein the at least one fluid-resistant region includes a fluid-resistant strip extending generally across a width of the at least one inner layer.

10. The reusable diaper of claim 9, wherein the fluid-resistant strip and the at least one outer layer are coupled together to generally define at least part of the waist portion.

11. The reusable diaper of claim 7, wherein:
    the waist portion is a first waist portion having two corner regions;
    the reusable diaper further comprises a second waist portion, the at least one fluid-resistant region being disposed adjacent the second waist portion; and
    the two corner regions of the first waist portion are releasably attachable to the second waist portion to secure the reusable diaper in a desired position, the two corner regions each being resiliently stretchable to permit at least some adjustability to the functional waist size of the reusable diaper as defined by the first and second waist portions when the first waist portion is releasably attached to the second waist portion.

12. The reusable diaper of claim 1, wherein the reusable diaper includes the first seam allowance and the second seam allowance, and wherein the reusable diaper further comprises:

a first stitch coupling the first layer of the at least one resiliently stretchable corner region and the at least one inner layer and generally defining the first seam allowance; and a second stitch coupling the second layer of the at least one resiliently stretchable corner region and the at least one outer layer and generally defining the second seam allowance.

13. The reusable diaper of claim 12, further comprising:
a top-stitch coupling the first seam allowance to the first layer of the at least one resiliently stretchable corner region; or
a top-stitch coupling the second seam allowance to the second layer of the at least one resiliently stretchable corner region.

14. The reusable diaper of claim 12, further comprising at least one top-stitch coupling at least one of:
the first seam allowance to the first layer of the at least one resiliently stretchable corner region; and/or
the second seam allowance to the second layer of the at least one resiliently stretchable corner region.

15. The reusable diaper of claim 1, wherein:
the reusable diaper includes the first seam allowance and a first top-stitch coupling the first seam allowance to the first layer of the at least one resiliently stretchable corner region; and/or
the reusable diaper includes the second seam allowance and a second top-stitch coupling the second seam allowance to the second layer of the at least one resiliently stretchable corner region.

16. The reusable diaper of claim 1, wherein the reusable diaper includes only the first seam allowance but not the second seam allowance.

17. The reusable diaper of claim 7, wherein the reusable diaper includes the first seam allowance and the second seam allowance, and wherein the reusable diaper further comprises:
a first stitch coupling the first layer of the corner region and the at least one inner layer and generally defining the first seam allowance; and
a second stitch coupling the second layer of the corner region and the at least one outer layer and generally defining the second seam allowance.

18. The reusable diaper of claim 17, further comprising:
a top-stitch coupling the first seam allowance to the first layer of the corner region; or
a top-stitch coupling the second seam allowance to the second layer of the corner region.

19. The reusable diaper of claim 17, further comprising at least one top-stitch coupling at least one of:
the first seam allowance to the first layer of the corner region; and/or
the second seam allowance to the second layer of the corner region.

20. The reusable diaper of claim 7, wherein:
the reusable diaper includes the first seam allowance and a first top-stitch coupling the first seam allowance to the first layer of the corner region; and/or
the reusable diaper includes the second seam allowance and a second top-stitch coupling the second seam allowance to the second layer of the corner region.

21. The reusable diaper of claim 7, wherein the reusable diaper includes only the first seam allowance but not the second seam allowance.

22. A reusable diaper comprising:
at least one inner layer configured to wick moisture;
at least one outer layer configured to be substantially impervious to liquids;
a waist portion generally defined by the at least one inner layer and the at least one outer layer, the waist portion having a corner region for use in securing the reusable diaper in a desired position;
the corner region including a first layer and a second layer coupled together so as to define an interior portion of the corner region, the first layer being further coupled to the at least one inner layer and the second layer being further coupled to the at least one outer layer;
wherein a first seam allowance is generally defined by the first layer of the corner region, the at least one inner layer, and a first stitch coupling the first layer of the corner region and the at least one inner layer, the first seam allowance being positioned generally within the interior portion of the corner region and extending generally away from the at least one inner layer;
wherein a second seam allowance is generally defined by the second layer of the corner region, the at least one outer layer, and a second stitch coupling the second layer of the corner region and the at least one outer layer and generally defining the second seam allowance, the second seam allowance being positioned generally within the interior portion of the corner region and extending generally away from the at least one outer layer;
wherein the reusable diaper includes at least one top-stitch coupling at least one of the first seam allowance to the first layer of the corner region or the second seam allowance to the second layer of the corner region;
whereby the positioning of the first and second seam allowances helps inhibit wicking of liquid through the seam allowances and into the corner region.

23. The reusable diaper of claim 22, wherein the at least one top-stitch comprises:
a first top-stitch coupling the first seam allowance to the first layer of the corner region; and
a second top-stitch coupling the second seam allowance to the second layer of the corner region.

24. The reusable diaper of claim 22, wherein the at least one top-stitch includes:
a first top-stitch coupling the first seam allowance to the first layer of the corner region; or
a second top-stitch coupling the second seam allowance to the second layer of the corner region.

* * * * *